US009132410B2

(12) United States Patent
Lively et al.

(10) Patent No.: US 9,132,410 B2
(45) Date of Patent: Sep. 15, 2015

(54) COMPOSITIONS, SYSTEMS AND METHODS FOR SEPARATING ETHANOL FROM WATER AND METHODS OF MAKING COMPOSITIONS FOR SEPARATING ETHANOL FROM WATER

(71) Applicant: Algenol Biofuels Inc., Fort Myers, FL (US)

(72) Inventors: Ryan Lively, Atlanta, GA (US); Michelle Dose, Austin, TX (US); Ronald Chance, Naples, FL (US); Benjamin McCool, Naples, FL (US)

(73) Assignee: Algenol Biotech LLC, Fort Myers, FL (US)

(*) Notice: Subject to any disclaimer, the term of this patent is extended or adjusted under 35 U.S.C. 154(b) by 68 days.

(21) Appl. No.: 14/145,897

(22) Filed: Dec. 31, 2013

(65) Prior Publication Data
US 2015/0182940 A1 Jul. 2, 2015

(51) Int. Cl.
*B01J 20/18* (2006.01)
*B01J 20/28* (2006.01)
*C12M 1/00* (2006.01)
*C01B 39/40* (2006.01)
*C07C 29/76* (2006.01)

(52) U.S. Cl.
CPC ............ *B01J 20/18* (2013.01); *B01J 20/28004* (2013.01); *C01B 39/40* (2013.01); *C07C 29/76* (2013.01); *C12M 21/02* (2013.01); *C12M 29/24* (2013.01)

(58) Field of Classification Search
CPC ..... B01J 20/18; B01J 20/28004; C01B 39/40; C07C 29/76
See application file for complete search history.

(56) References Cited

U.S. PATENT DOCUMENTS

| | | |
|---|---|---|
| 4,420,561 A | 12/1983 | Chen et al. |
| 4,442,210 A | 4/1984 | Dessau et al. |
| 4,515,892 A | 5/1985 | Chen et al. |
| 6,358,301 B1 | 3/2002 | Fleck |
| 6,838,406 B2 | 1/2005 | Balducci et al. |
| 7,214,637 B2 | 5/2007 | Balducci et al. |
| 7,435,699 B2 | 10/2008 | Jolimaitre et al. |
| 7,547,778 B2 | 6/2009 | Balducci et al. |
| 8,133,308 B2 | 3/2012 | Lively et al. |
| 8,163,066 B2 | 4/2012 | Eisenberger |
| 8,491,705 B2 | 7/2013 | Choi et al. |
| 2009/0025555 A1 | 1/2009 | Lively et al. |
| 2011/0041688 A1 | 2/2011 | Eisenberger |
| 2011/0179948 A1 | 7/2011 | Choi et al. |

OTHER PUBLICATIONS

Zhang et al., Langmuir, (2012), 28, pp. 8664-8673, published on May 8, 2012.*

Zhang et al., Langmuir, (2012), 28, p. 8664-8673, published on May 8, 2012.*
Muller et al., "High-resolution sorption studies of argon and nitrogen on large crystals of microporous zeolite ZSM-5", Frensenius Z Analytische Chemie, vol. 333 (1989) 433-436.
Carmo et al., "Ethanol-water adsorption on commercial 3A zeolites: kinetic and thermodynamic data", Brazilian Journal of Chemical Engineering, vol. 14, No. 3 (1997).
Milestone et al., "Concentration of Alcohols by Adsorption of Silicalite", Journal of Chemical Technology and Biotechnology, vol. 31 (1981) 732-736.
Akcay et al., "Wet ball milling of zeolite HY", Powder Technology, vol. 142 (2004) 121-128.
Park, S.; Jiang, N. Morphological Synthesis of Zeolites. In Zeolites and Catalysis. J Cejka, A Corma, S Zones. Weinheim, Germany: Wiley-VCH Verlag GmbH, 2010, pp. 131-150.
Sing, K. S. W.; Everett, D. H.; Haul, R. A. W.; Moscou, L.; Pierotti, R. A.; Rouquerol, J.; Siemieniewska, T. Reporting physisorption data for gas/solid systems with special reference to the determination of surface area and porosity. I. U. P. A. C. 1985, 57 (4), pp. 603-619.
Karger, J.; Ruthven, D.; Theodorou, D. Medium-Pore (Ten-Ring) Zeolites. In Diffusion in Nanoporous Materials. Wilely-VCH Verlag GmbH & Co, Weinheim, Germany. 2011. DOI: 10.1002/9783527651276.ch18.
Dose, M.; Zhang, K.; Thompson, J.; Leisen, J.; Chance, R.; Koros, W.; McCool, B.; Lively, R. "Effect of Crystal Size on Framework Defects and Water Uptake in Fluoride Mediated Silicate-1", Chemistry of Materials, vol. 26 (2014), 4368-4376.
Zhang et al., "Adsorption of Water and Ethanol in MFI-Type Zeolites", Langmuir, vol. 28 (2012), 8664-8673.
Gualtieri et al., "Seeded growth of TPA-MFI films using the fluoride route", Microporous and Mesoporous Materials, vol. 111 (2008), 604-611.
Trzpit et al., "The Effect of Local Defects on Water Adsorption in Silicalite-1 Zeolite: A Joint Experimental and Molecular Simulation Study", Langmuir, vol. 23 (2007), 10131-10139.
Zhang et al., "Diffusion of Water and Ethanol in Silcalite Crystals Synthesized in Fluoride Media", Microporous and Mesoporous Materials, vol. 170 (2012), 259-265.
Lively et al., "Ethanol and water adsorption in methanol-derived ZIF-71", Chemical Communications vol. 47 (2011), 8667-8669.
Zhang et al., "Alcohol and water adsorption in zeolitic imidazolate frameworks", Chemical Communications, vol. 49 (2013), 3245-3247.
Zhang et al., "Investigating the Intrinsic Ethanol/Water Separation Capability of ZIF-8: An Adsorption and Diffusion Study", The Journal of Physical Chemistry C, vol. 117 (2013), 7214-7225.
Camblor et al., "Synthesis of all-silica and high-silica molecular sieves in fluoride media" Topics in Catalysis, vol. 9 (1999), 59-76.
Bai et al., "Multicomponent Adsorption of Alcohols onto Silicalite-1 from Aqueous Solution: Isotherms, Structural Analysis, and Assessment of Ideal Adsorbed Solution Theory", Langmuir, vol. 28 (2012), 15566-15576.
Mallon et al., "Probing the Relationship between Silicalite-1 Defects and Polyol Adsorption Properties", Langmuir, vol. 29 (2013), 6546-6555.
Xiong et al., "Molecular Screening of Alcohol and Polyol Adsorption onto MFI-Type Zeolites", Langmuir, vol. 28 (2012), 4491-4499.
Agger et al., "Silicalite Crystal Growth Investigated by Atomic Force Microscopy", Journal of the American Chemical Society, vol. 125 (2003), 830-839.

(Continued)

Primary Examiner — Yong Chu
(74) Attorney, Agent, or Firm — David J. Lorenz

(57) ABSTRACT

Silicalite particles, methods of making silicalite particles, systems comprising silicalite particles and methods for using silicalite particles to separate ethanol from water.

3 Claims, 16 Drawing Sheets

(56) References Cited

OTHER PUBLICATIONS

Kortunov et al., "Influence of Defects on the External Crystal Surface on Molecular Uptake into MFI-type Zeolites", Chemical Matter, vol. 16 (2004), 3352-3558.

Karwacki et al., "Morphology-dependent zeolite intergrowth structures leading to distinct internal and outer-surface molecular diffusion barrier", Nature Materials, vol. 8 (2009), 959-965.

Chezeau et al., "High-resolution solid-state Sl and C n.m.r on highly siliceous MFI-type zeolites synthesized in nonalkaline fluoride medium", Zeolites, vol. 9 (1989), 78.

Xomeritakis et al., "Growth, microstructure, and permeation properties of supported zeolite (MFI) films and membranes prepared by secondary growth", Chemical Engineering Science, vol. 54 (1999), 3521-3531.

Bonilla et al., "Zeolite (MFI) Crystal Morphology Control Using Organic Structure-Directing Agents", Chemical Matter, vol. 16 (2004), 5697-5705.

Hay et al., "Orthorhombic-Monoclinic Phase Changes in ZSM-5 Zeolite/Silicalite", Chemical Communications, vol. 21 (1984), 1433.

Hay et al., "Examination of the Monoclinic/Orthorhombic Transition in Silicslite Using XRD and Silicon NMR", The Journal of Physical Chemistry Letters C, vol. 89 (1985), 1070-1072.

Cheng et al., "Functionalization of the Internal Surface of Pure-Silica MFI Zeolite with Aliphatic Alcohols", The Journal of Physical Chemistry Letters C, vol. 112 (2008), 3543-3551.

Llewellyn et al., "A Microcalorimetric study of the different states of argon and nitrogen adsorbed at 77K on silicalite-1 and ZSM-5", Journal of Thermal Analysis, vol. 38 (1992), 683-92.

Llewellyn et al., "On the physisorption isotherm of the MFI-type zeolites: the high pressure hysteresis", Microporous Materials, vol. 1 (1993), 247-256.

Llewellyn et al., "Adsorption by Mfi-type zeolites examined by isothermal microcalorimetry and neutron diffraction. 2 Nitrogen and carbon monoxide", Langmuir, vol. 9 (1993), 1852-1856.

Nakai et al., "High resolution adsorption isotherms of N2 and Ar for nanoporous silicas and MFI zeolites", Adsorption, vol. 13 (2007), 351-356.

Garcia-Perez et al., "Unraveling the argon adsorption process in MFI-type zeolites", The Journal of Physical Chemistry Letters C, vol. 112 (2008), 9976-9979.

Lukens et al., "Evaluating Pore Sizes in Mesoporous Materials: A simplified Standard Adsorption Method and a Simplified Broekhoff-de Boer Method", Langmuir, vol. 15 (1999), 5403-5409.

Sircar et al., "Recent developments in macroscopic measurement of multicomponent gas adsorption equilibria, kinetics, and heats", Industrial and Engineering Chemistry Research, vol. 46 (2007), 2817-2927.

Krishna et al., "Hydrogen Bonding Effects in Adsorption of Water-Alcohol Mixtures in Zeolites and the Consequences for the characterization of the Maxwell-Stefan Diffusivities", Langmuir, vol. 26 (2010), 10854-10867.

Dose, M.; Zhang, K.; Thompson, J.; Leisen, J.; Chance, R.; Koros, W.; McCool, B.; Lively, R. "Supporting Information for Effect of Crystal Size on Framework Defects and Water Uptake in Fluoride Mediated Silicate-1", Chemistry of Materials, vol. 26 (2014), 4368-4376.

* cited by examiner

COMPOSITIONS, SYSTEMS AND METHODS FOR SEPARATING ETHANOL FROM WATER AND METHODS OF MAKING COMPOSITIONS FOR SEPARATING ETHANOL FROM WATER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND

Recent developments in the biofuel industry have related to the use of genetically enhanced microorganisms to make products such as ethanol, typically in dilute solutions with water. Various efforts and different approaches have been undertaken to efficiently separate ethanol from water and enrich the ethanol product.

U.S. Pat. No. 8,163,066 to Eisenberger concerns selectively moving a vertically oriented carbon dioxide capture structure supporting an amine sorbent into and out of a regeneration enclosure in order to remove carbon dioxide from ambient air.

U.S. Pat. No. 8,491,705 to Choi et al. concerns capture of carbon dioxide from ambient air using solid amine adsorbents tethered to a silica, metal oxide or polymer resin substrate through covalent bonding.

Zhang et al., "Adsorption of Water and Ethanol in MFI-Type Zeolites", Langmuir 2012, 28, 8664-8673 concerns water and ethanol vapor adsorption on MFI-type zeolites and discloses the preparation of silicalite-1($F^-$) in a fluoride-mediated route by hydrothermal synthesis adapted from literature procedures.

Gualtieri et al., "Seeded growth of TPA-MFI films using the fluoride route", Microporous and Mesoporous Materials 111 (2008) 604-611 concerns the preparation of TPA-MFI films on dense amorphous silica glass supports using the fluoride route in combination with surface seeding.

A need exists for an improved sorbent that provides decreased water uptake and enhanced selectivity of ethanol over water.

SUMMARY

An object of the present invention is a silicalite MFI particle having a mean height or b-dimension of about 0.2 microns to about 10 microns, a mean aspect ratio of about 5 to about 14, pore volume of less than about 0.0025 $cm^3$ per gram, water uptake of about 0.20 mmol per gram or less at an activity of 0.98 and 35° C., and selectivity for ethanol over water of about 190 at an ethanol mole fraction of about 0.2 in a vapor-phase ethanol/water mixture.

Another object of the present invention is a method for making silicalite MFI particles having a mean height or b-dimension of about 0.2 microns to about 10 microns, a mean aspect ratio of about 5 to about 14, pore volume of less than about 0.0025 $cm^3$ per gram, water uptake of about 0.20 mmol per gram or less at an activity of 0.98 and 35° C., and selectivity for ethanol over water of about 190 at an ethanol mole fraction of about 0.2 in a vapor-phase ethanol/water mixture.

Another object of the present invention is a system for separating ethanol from water comprising silicalite MFI particles having a mean height or b-dimension of about 0.2 microns to about 10 microns, a mean aspect ratio of about 5 to about 14, pore volume of less than about 0.0025 $cm^3$ per gram, water uptake of about 0.20 mmol per gram or less at an activity of 0.98 and 35° C., and selectivity for ethanol over water of about 190 at an ethanol mole fraction of about 0.2 in a vapor-phase ethanol/water mixture.

Another object of the present invention is a method for separating ethanol from water using silicalite MFI particles having a mean height or b-dimension of about 0.2 microns to about 10 microns, a mean aspect ratio of about 5 to about 14, pore volume of less than about 0.0025 $cm^3$ per gram, water uptake of about 0.20 mmol per gram or less at an activity of 0.98 and 35° C., and selectivity for ethanol over water of about 190 at an ethanol mole fraction of about 0.2 in a vapor-phase ethanol/water mixture.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE SEVERAL VIEWS OF THE DRAWING

Embodiments of the invention will be described below with reference to the following figures.

DETAILED DESCRIPTION

Figure 1:
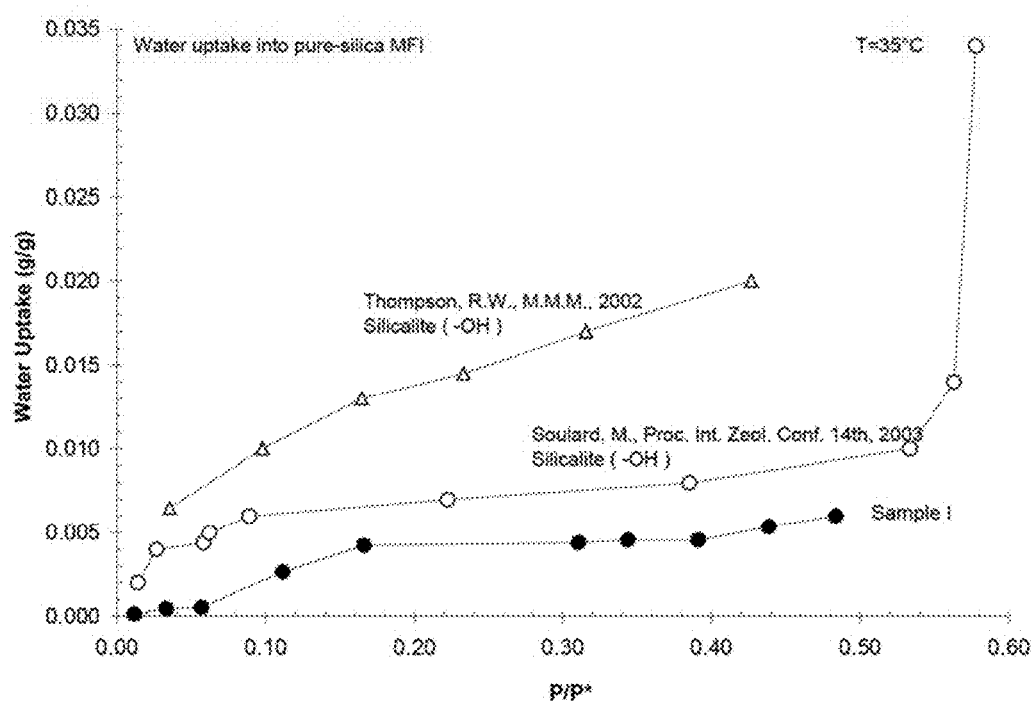
FIG. 1 shows water uptake for silicalite particles made according to the present invention and selected silicalite particles made according to methods known in the art.

As used herein, the term "silicalite" means a polymorph of silica having a zeolite structure, but with no aluminum content detectable by energy-dispersive X-ray spectroscopy conducted using, for example, Oxford Instruments EDS analysis or similar suitable instrument.

As used herein, the term "silica" means silicon dioxide, a chemical compound that is an oxide of silicon with the chemical formula $SiO_2$.

As used herein, the term "zeolite" means a microporous, aluminosilicate mineral commonly used as a commercial adsorbent.

As used herein, the term "microporous" means a material containing pores with diameters less than 0.002 microns, such as zeolites and metal-organic frameworks.

As used herein, the term "mesoporous" means a material containing pores with diameters between 0.002 and 0.050 microns.

As used herein, the term "aluminosilicate mineral" means a mineral composed of aluminium, silicon, and oxygen, plus countercations.

As used herein, the term "silicate" means a compound containing an anionic silicon compound.

As used herein, the term "mineral" means a naturally occurring substance that is solid and stable at room temperature, representable by a chemical formula, usually abiogenic, and has an ordered atomic structure.

As used herein, the term "abiogenic" means lacking carbon and hydrogen atoms.

As used herein, the term "sorbent" means a material used to absorb or adsorb liquids or gases.

As used herein, the term "adsorbent" means a material on which atoms, ions or molecules of a gas, liquid or dissolved solid can adhere.

As used herein, the term "MFI" means mordenite framework inverted.

As used herein, the term "mordenite" means a zeolite mineral with the chemical formula, $(Ca, Na_2, K_2)Al_2Si_{10}O_{24} \cdot 7H_2O$.

As used herein, the term "framework inverted" means a topology that is defined by the negative space, interstitial space or pore space, of another zeolite topology.

As used herein, the term "particle" means a solid material whose constituent atoms, molecules, or ions are arranged in an ordered pattern extending in the a, b and c spatial dimensions, as illustrated in FIG. 2(f).

As used herein, the term "F-MFI" means MFI crystalline zeolites formed from fluoride-containing silicate gels.

As used herein, the term "defect-free" means amorphous defects less than about 0.1% as measured by X-ray diffraction conducted using, for example, a PANalytical X'Pert PRO Materials Research Diffractometer or similar suitable instrument; metal center defects less than about 0.001% as measured by energy-dispersive X-ray spectroscopy conducted using, for example, Oxford Instruments EDS analysis or similar suitable instrument; and silanol defects measured by water loading at unit activity of less than about 0.98 for a material with pore volume greater than about 0.15 cubic centimeters per gram, the measure of which is equivalent to less than about 0.1 silanol defects per unit cell of a MFI particle.

As used herein, the term "fiber" means a slender, elongated, threadlike object or structure.

As used herein, the term "monolith sorbent reactor" means inorganic rods or cylinders having surfaces coated with a sorbent, or alternatively honey-comb inorganic structures having inner surfaces coated with a sorbent.

As used herein, the term "interstice" means an empty space or gap between spaces full of structure or matter.

As used herein, the term "selectivity" means the ability of a sorbent to discriminate between an isolate in a mixture and the other components of the mixture and to retain the isolate exclusive of the other mixture components. Selectivity is a function of the chemical structure of the isolate, the properties of the sorbent, and the composition of the mixture, with maximum selectivity achieved when a sorbent is chosen that interacts through isolate functional groups that are not common to other mixture components.

As used herein, the term "isolate" means a chemical species or product of interest that is separated by a sorbent from a mixture.

As used herein, the term "water uptake" means water sorbed within a microporous material under exposure to water at certain relative pressures and temperatures.

As used herein, the term "non-wetting" means, in reference to a porous material exposed to 100% relative humidity water vapor or liquid water at 1 bar, the absence of liquid water in the pores.

As used herein, the term "hydrophobic" means uptake by a microporous material of less than 0.5 mmol/g water at 100% relative humidity water and 35° C.

As used herein, the term "space velocity" means the quotient of the entering volumetric flow rate of reactants divided by the reactor or catalyst bed volume, which indicates the number of reactor volumes of feed that can be treated in a unit time.

As used herein, the term "gel" means a substantially dilute cross-linked system present as a solid, jelly-like material that exhibits no flow when in steady-state.

As used herein, the term "homogeneous" means substances and mixtures that are in a single phase.

As used herein, the term "amorphous" means lacking the order characteristic of a crystal or micro-crystalline substance.

As used herein, the term "colloid" means a substance microscopically dispersed throughout another substance.

As used herein, the term "vacuum filtration" means a technique for separating a solid product from a solvent or liquid reaction mixture in which the mixture of solid and liquid is poured through a filter in, most commonly, a funnel.

As used herein, the term "sonication" means applying sound energy to agitate particles in a sample in order to initiate crystallization processes, control polymorphic crystallizations, and/or intervene in anti-solvent precipitations (crystallization) to aid mixing and isolate small crystals.

As used herein, the term "centrifugation" means the use of centrifugal force for the sedimentation of mixtures with a centrifuge.

As used herein, the term "decantation" means a process for the separation of mixtures, by removing a top layer of liquid from which a precipitate has settled.

As used herein, the term "drying" means a mass transfer process consisting of the removal of water or another solvent by evaporation from a solid, semi-solid or liquid.

As used herein, the term "calcination" means a thermal treatment process in presence of air applied to ores and other solid materials to bring about a thermal decomposition, phase transition, or removal of a volatile fraction.

As used herein, the term "ball-milling" means grinding materials into powder.

As used herein, the term "monoclinic" means a crystal described by three vectors of unequal length forming a rectangular prism with a parallelogram as its base, such that two pairs of vectors are perpendicular, while the third pair makes an angle other than 90°.

As used herein, the term "orthorhombic" means a crystal described by three vectors that remain mutually orthogonal to form a rectangular prism with a rectangular base and height, such that the length, width and height are distinct.

As used herein, the term "unit cell" means the space enclosed by the points of a lattice defining a crystal structure and is the simplest repeating unit that defines the crystal structure. The unit cell is specified by three vectors, a, b and c that form the edges of a parallelepiped. The lengths of a, b and c are called the unit cell dimensions, and their directions define the major crystallographic axes.

As used herein, the term "b-dimension" is illustrated in FIG. 2(f) and is the smallest in magnitude of the a (width), b (height) and c (length) spatial dimensions of a silicalite particle of the present invention.

As used herein, the term "pore volume" means a measure of void spaces in a porous material. Pore volume of materials such as silicalite and zeolites is commonly measured on the basis of nitrogen absorption capacity of the material at low temperature and high pressure. More specifically, pore volume can be determined using nitrogen as a probe gas at 77 K via, for example, a Micrometrics ASAP 2020 adsorption porosimeter or similar suitable instrument equipped with analysis functions for estimating BET pore volumes by the Horvath-Kawazoe method.

As used herein, the term "about" means approximately, in the region of, roughly, or around. When the term "about" is used in conjunction with a numerical value or range, it modifies that value or range by extending the boundaries above and below the numerical value(s) set forth. In general, the term "about" is used herein to modify a numerical value(s) above and below the stated value(s) within a confidence interval of 90% or 95%.

The present invention relates to improved silicalite particles having decreased water uptake, methods for making the improved silicalite particles, systems for separating ethanol from water comprising the improved silicalite particles and methods for separating ethanol from water using the improved silicalite particles. These and other aspects of the present invention significantly reduce energy consumption, and operating costs related thereto, vis-a-vis current ethanol/water separation processes.

Silicalite particles of the present invention are made from a mixture of tetrapropylammonium bromide and ammonium fluoride dissolved in water, to which amorphous, colloidal silicon dioxide is added, resulting in the formation of a homogeneous gel. The homogeneous gel is heated to produce the silicalite particles.

According to the present invention, the size and morphology of the silicalite particles can be altered by, in various embodiments, dispersing silicalite seeds in the mixture of tetrapropylammonium bromide and ammonium fluoride in order to impose structure on the formation of the homogenous gel, aging the homogenous gel before heating, and/or varying the duration of heating of the homogenous gel.

In some embodiments, silicalite particles of the present invention have a mean height, b, of about 0.2 microns to about 40 microns. In some embodiments, silicalite particles of the present invention have a mean height, b, of about 0.2 microns to about 10 microns. In some embodiments, silicalite particles of the present invention have a mean aspect ratio of about 5 to about 20. In some embodiments, silicalite particles of the present invention have a mean aspect ratio of about 5 to about 14.

According to the present invention, silicalite particles of the present invention are distinguishable from sorbents known in the art using, in some embodiments, X-ray diffraction, energy dispersive X-ray spectroscopy and $^{29}$Si MAS NMR to show the absence of amorphous defects, metal center defects and silanol defects, respectively, in silicalite particles of the present invention and the presence of such defects in sorbents known in the art. Silicalite particles of the present invention are also distinguishable from sorbents known in the art by their lack of defect-related water absorption and their unexpectedly large ethanol/water selectivities.

Figure 9:
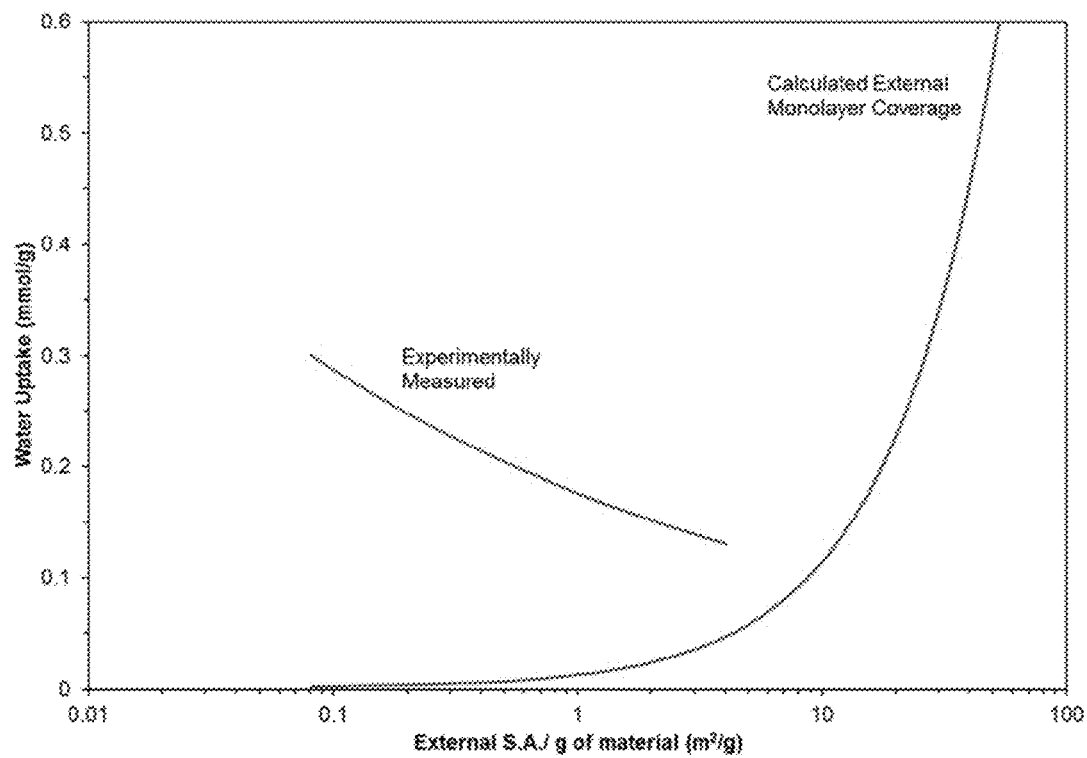
FIG. 9 shows a plot of measured water uptake at 95% and 35° C. activity for silicalite particles made according to the present invention and estimated external monolayer water sorption as a function of ratio of external surface area per gram of sample.
Figure 10:
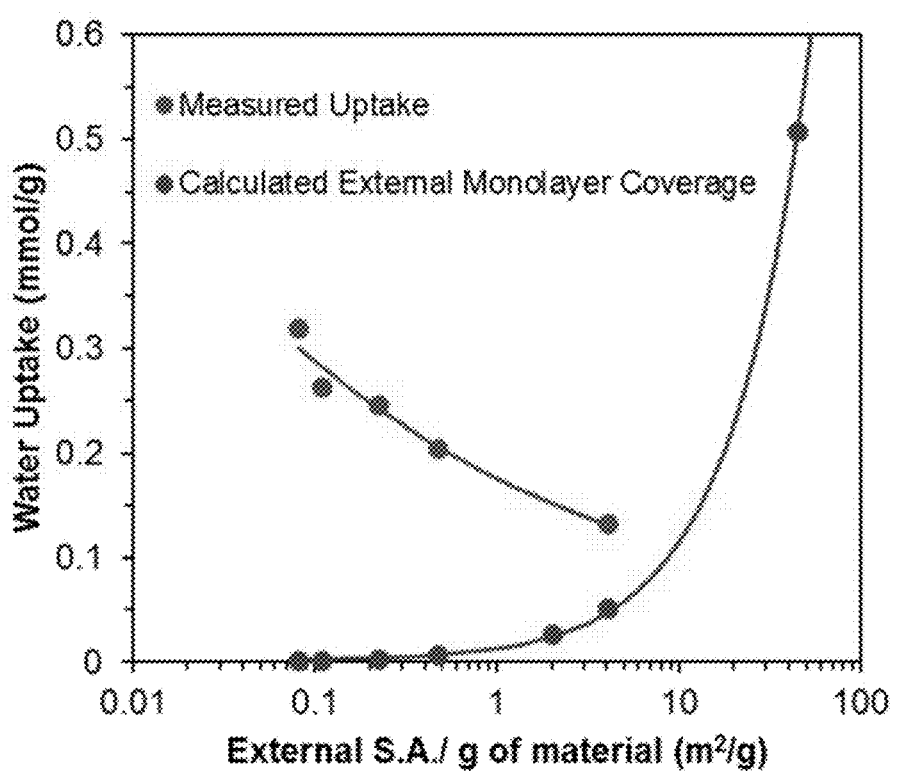
FIG. 10 shows a plot of measured water uptake at 95% and 35° C. activity for silicalite particles made according to the present invention and estimated external monolayer water sorption as a function of ratio of external surface area per gram of sample.

Silicalite particles of the present invention provide decreased water uptake and increased selectivity for ethanol over water, and corresponding improved energy efficiency of separation processes utilizing sorbents comprising silicalite particles of the present invention, in comparison with silicalite particles known in the art. As shown in FIGS. 9 and 10, water uptake by silicalite particles of the present invention unexpectedly decreases with decreasing particle size. Without wishing to be bound by theory, smaller silicalite particles of the present invention may have more predominantly monoclinic unit cells and fewer orthorhombic unit cells that create mesoporous fissures at the interfaces between monoclinic and orthorhombic unit cells in comparison with larger silicalite particles. According to the present invention, the mesoporous fissures permit capillary condensation of water in silicalite particles, thereby increasing water uptake by the particles, and are present in higher concentrations in larger silicalite particles.

Figure 8:
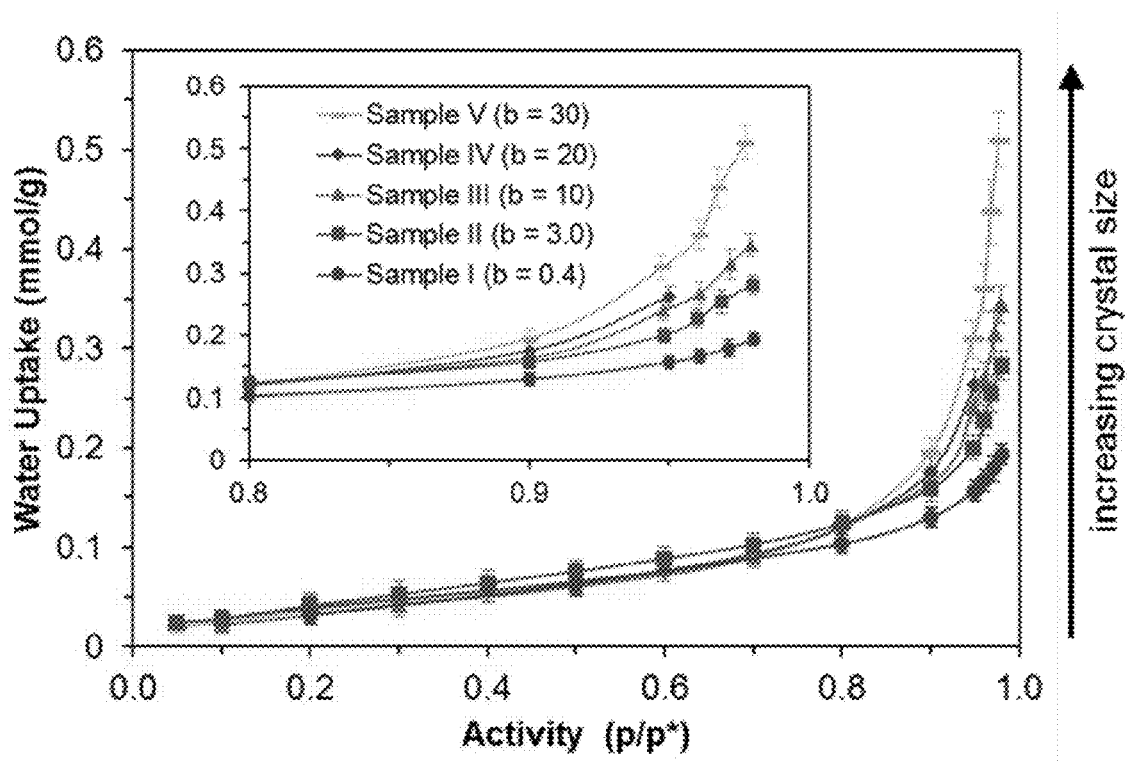
FIG. 8 shows a plot of water vapor adsorption at 35° C. for silicalite particles made according to the present invention.

FIG. 1 shows a comparison of water uptake between silicalite particles made according to the present invention, specifically silicalite particles of Sample I described below, and selected silicalite particles known in the art, with silicalite particles made according to the present invention consistently showing decreased water uptake. In some embodiments, as shown in FIG. 8, water uptake of silicalite particles of the present invention is about 0.20 mmol per gram or less at an activity of 0.98 and 35° C.

Figure 13:
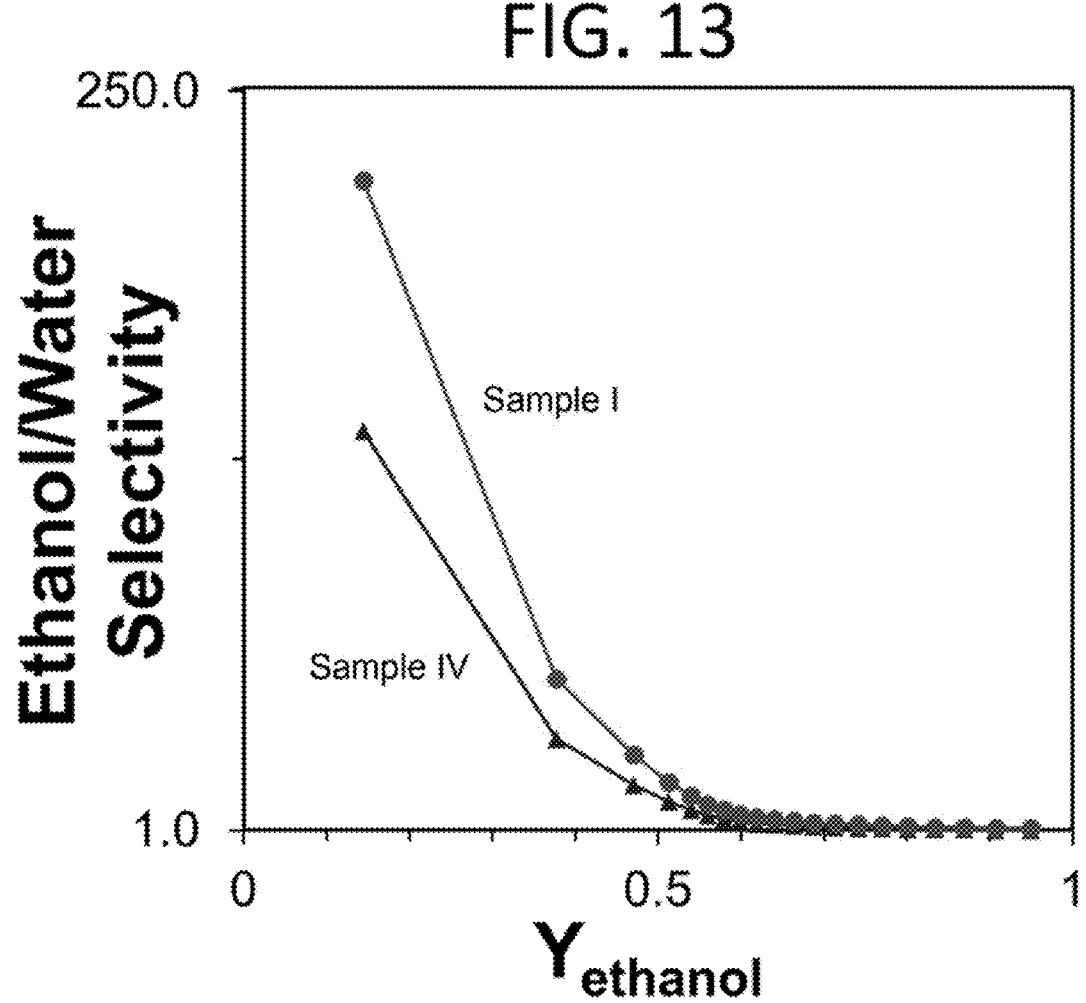
FIG. 13 shows a plot of ethanol/water selectivity.

In some embodiments, as shown in FIG. 13, selectivity of silicalite particles of the present invention for ethanol over water is about 190 at an ethanol mole fraction of about 0.2 in a vapor-phase ethanol/water mixture.

Low water uptake and high ethanol/water selectivity provided by silicalite particles of the present invention advantageously increase the efficiency and concomitantly reduce the energy requirements of separating ethanol from water. An adsorption process using silicalite particles of the present invention reduces the energy consumed in the process of separating ethanol from water by shifting the thermal energy requirement driving the separation from the heat of vaporization of water, which has a value known the art of about 2,260 kJ/kg, to the heat of sorption of ethanol, which has a value known the art of about 845 kJ/kg. Shifting the thermal energy requirement to ethanol, which is dilute at concentrations of about 1 wgt % or less in aqueous liquid or vapor streams of interest in the present invention, reduces energy requirements relative to traditional distillation techniques, since such techniques are directed to vaporization of water from a stream that contains primarily water. An approach utilizing silicalite particles of the present invention therefore is directed to a component of an aqueous stream that has a lower heat of vaporization and is present in smaller amounts in the dilute stream, thereby deleveraging the energy requirements for separating the components.

A gas delivery system can advantageously be paired with a system that uses silicalite particles of the present invention to recover ethanol from a dilute stream. In some embodiments, after the silicalite particles are washed with a mixture of ethanol and water in liquid or vapor form and the silicalite particles adsorb ethanol from the mixture, the silicalite particles subsequently are washed with carbon dioxide as a sweep gas and heated to a preselected temperature in a desorption step, during which ethanol desorbs from the silicalite particles into the carbon dioxide. The desorbed ethanol can then, for example, be condensed to a liquid product, optionally after passing through an ethanol dehydration membrane. Excess carbon dioxide from the gas delivery system can be sent to a photobioreactor containing an algae culture that requires carbon as a feedstock.

After desorption, the silicalite particles are washed with water, and carbon dioxide partitions into the water as dissolved carbon. The carbon dioxide-enriched aqueous stream can be sent to the photobioreactor for consumption by the algae culture as a carbon feedstock.

Silicalite particles of the present invention can be bound into a sorbent having a hollow fiber form using a hydrophobic, polymer binder in a spinning process and incorporated in a monolith sorbent reactor that is used in the ethanol/water processes described herein. One of ordinary skill in the art will appreciate that using the sorbent in this form will help reduce pressure losses as liquid and vapor streams are pumped through the fiber bed, which will reduce costs associated with pumping the streams.

A fiber sorbent bed of the present invention can be used to treat either liquid or vapor streams leaving a photobioreactor, or, for example, leaving a scrubber or other process operations used to capture ethanol product from the photobioreactor.

Example 1

Silicalite particles identified as Samples I-V were synthesized by fluoride-mediated reaction routes with varying reaction conditions to achieve varying particle dimensions. Reagent quantities and other parameters for Samples I-V are specified in Table 1.

Reaction Routes:

1. For Sample I, disperse silica seed particles in deionized water in a polytetrafluoroethylene container using a sonication horn operated for three bursts of 30 seconds per burst.

2. For Samples I-V, dissolve tetrapropylammonium bromide ("TPABr"; 99% Sigma Aldrich) and ammonium fluoride ("NH$_4$F"; >99.99% Sigma Aldrich) in the deionized water in the polytetrafluoroethylene container, covered and stirred for 10 minutes at room temperature.

3. For Samples I-V, add Cab-O-Sil® M-5 (untreated fumed silica; Cabot Corporation) to the mixture, stirring manually for 10 minutes to form a homogeneous gel.

4. For Sample III, age the gel covered with Parafilm using an automated impeller.

5. For Samples I-V, seal the gel in a polytetrafluoroethylene sleeve in a stainless steel Parr reactor and react the gel in an oven preheated to 180° C.

6. For Samples I-V, cool the resulting solids for about 8 hours.

7. For Samples I-V, vacuum filter the resulting solids and wash with at least 200 mL of deionized water.

8. For Samples I-V, add 30 mL of deionized water to the solids and sonicate for 90 seconds to remove any un-reacted silica.

9. For Samples I-V, centrifuge the slurry and decant off the water.

10. For Samples I-V, repeat steps 8 and 9 at least twice.

11. For Samples I-V, dry the solids at 110° C. under vacuum.

12. For Samples I-V, calcine the solids according to the following profile: increase 5° C./min from 25° C. to 120° C., hold 120° C. for 2 hrs, ramp 5° C./min to 550° C., hold 550° C. for 12 hrs.

Silicalite seed particles used in step 1 above for Sample I were made according to the reaction route for Sample IV and were ball milled in about 1 mL of deionized water for 5 min in a Spex 8000M Mixer/Mill® using a hardened steel grinding vial with two 0.5 inch steel balls.

TABLE 1

| Sample | DI water (g) | Seeds (g) | TPABr (g) | NH$_4$F (g) | Cab-O-Sil (g) | Aging time (hours) | Reaction time (days) | Yield (g) |
|---|---|---|---|---|---|---|---|---|
| I | 13.44 | 25 | 0.81 | 0.059 | 2.24 | 0 | 4 | 1.748 |
| II | 13.44 | 0 | 0.81 | 0.059 | 2.24 | 0 | 4 | 0.828 |
| III | 13.44 | 0 | 0.81 | 0.059 | 2.24 | 20 | 14 | 1.38 |
| IV | 13.44 | 0 | 0.81 | 0.059 | 2.24 | 0 | 14 | 1.7 |
| V | 13.44 | 0 | 0.608 | 0.059 | 2.24 | 0 | 14 | 1.4 |

Example 2

Scanning electron microscopy (SEM) was used to evaluate the particle size and morphology of Samples I-V. The samples were sputter-coated with a 10-20 nm thick gold coating (Model P-S1; ISI, Mountain View, Calif.), and transferred to a high-resolution field emission scanning electron microscope (Leo 1530, Leo Electron Microscopy, Cambridge, UK).

Figure 2:
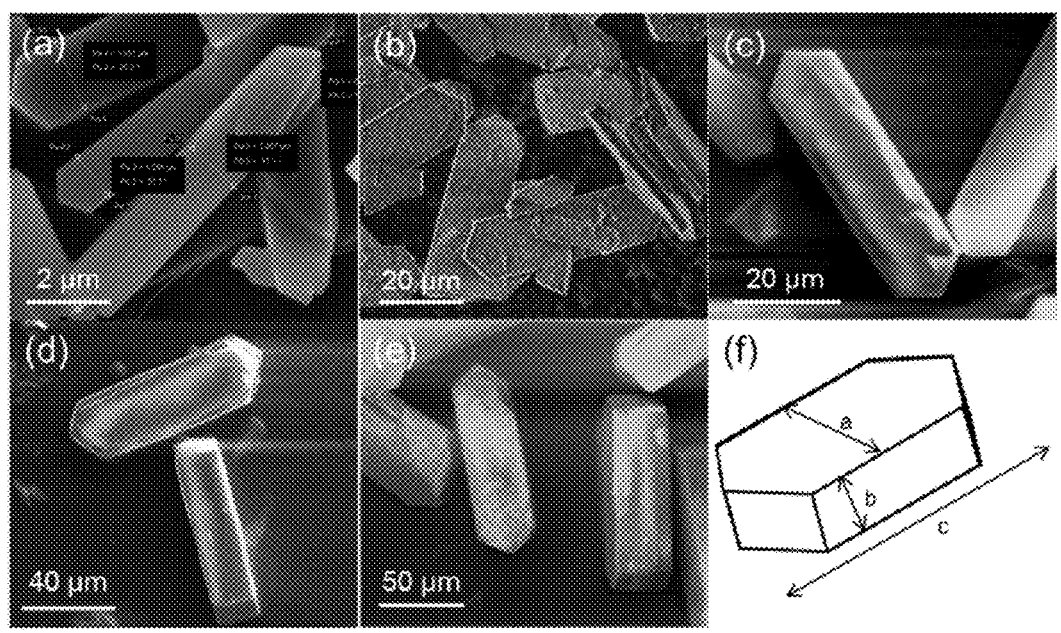
FIGS. 2(a)-(e) show scanning electron microscope micrographs of silicalite particles made according to the present invention.
FIG. 2(f) shows representational axes of silicalite particles made according to the present invention.

As shown in FIG. 2, each Sample exhibited coffin-shaped morphology. Measurements of a, b and c dimensions in Table 2 are averages.

TABLE 2

| Sample | FIG. 2 image | a (μm) | b (μm) | c (μm) | Aspect Ratio |
|---|---|---|---|---|---|
| I | (a) | 1.5 | 0.4 | 9.0 | 13 |
| II | (b) | 15 | 3.0 | 50 | 11 |
| III | (c) | 15 | 10 | 55 | 3.5 |
| IV | (d) | 30 | 20 | 80 | 2.8 |
| V | (e) | 35 | 30 | 120 | 2.6 |

Aspect Ratio=$(a+c)+2b$.

Example 3

X-ray diffraction was conducted on the silicalite particles of Samples I-V to identify MFI topology and to investigate the particles' lattice systems. Powder x-ray diffraction was performed at room temperature on an X'Pert Pro PAnalytical X-ray Diffractometer using Cu—Kα radiation. Measurements were carried out from 5-40° 2θ, using an X'celerator detector with low-background sample holders.

Figure 3:
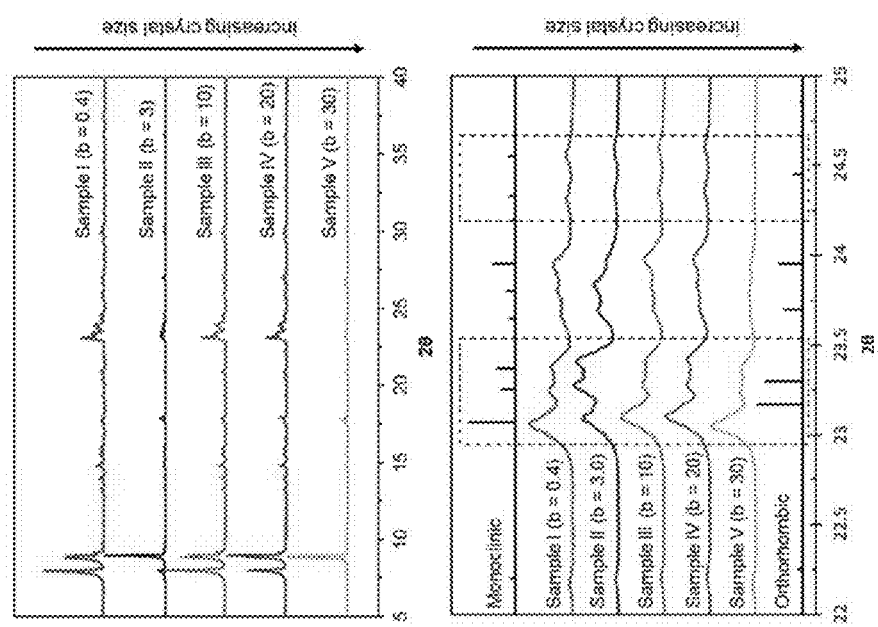
FIG. 3 shows a plot of X-ray diffraction patterns for silicalite particles made according to the present invention.

X-ray diffraction patterns shown in FIG. 3 confirmed that Samples I-V were crystalline with a MFI-type framework topology. Doublet diffraction peaks observed between 24.3-24.6° 2θ for monoclinic MFI-type crystals weakened in intensity from the smallest Sample I particles to the largest Sample V particles, for which only trace peaks of the monoclinic phase were observed. Triplet diffraction peaks associated with monoclinic symmetry observed between 23.0-23.4° and 23.6-24.0° 2θ were more defined for the smaller particles, such as Sample I, indicating that smaller particles were predominately monoclinic phase, while the larger particles were increasingly orthorhombic phase.

Example 4

$^{29}$Si MAS NMR measurements of Samples I, II, IV and V were performed on a BSX300 spectrometer operating at 59.64 MHz with a spinning rate of 5 kHz. Spectra were acquired using a 7 mm probe with $ZrO_2$ rotors and a 10-second recycle delay. Chemical shifts were referenced using 3-(trimethylsilyl)-1 propanesulfonic acid sodium salt.

Figure 4:
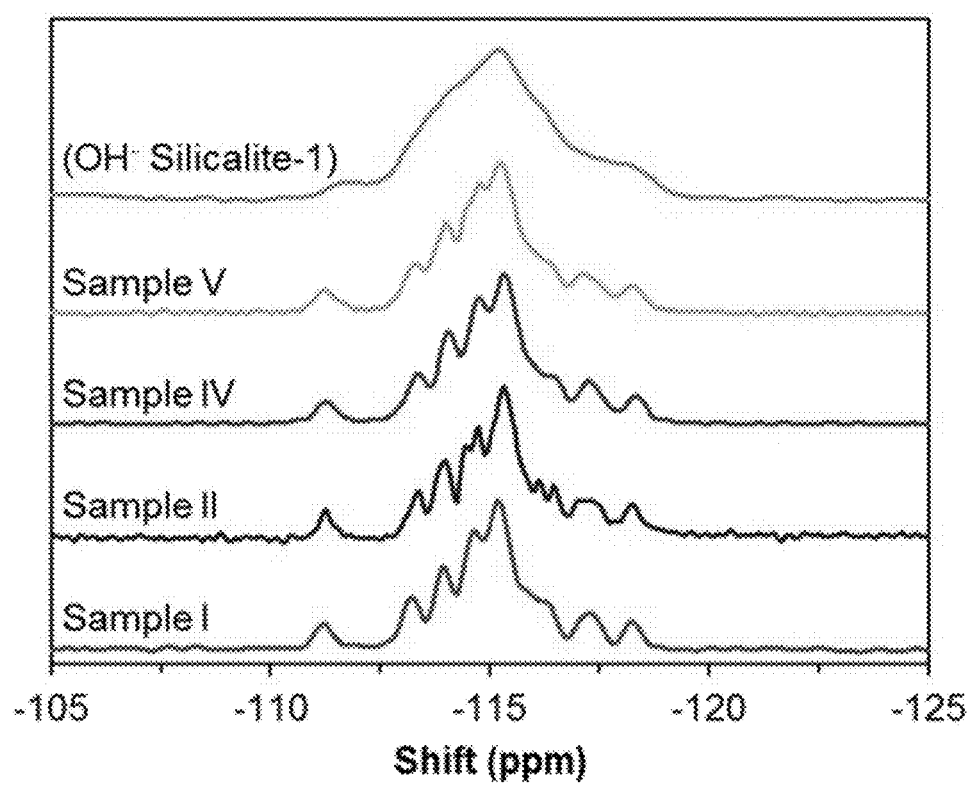
FIG. 4 shows a plot of $^{29}Si$ MAS NMR spectra for silicalite particles made according to the present invention.

The $^{29}$Si NMR spectra shown in FIG. 4 for the silicalite particles of Samples I, II, IV and V exhibited 8 to 10 sharp peaks between −110 and −120 ppm, corresponding to the $Q^4$ groups (Si—[(OSi)$_4$]) and were assigned to 24 distinct crystallographic silicon sites. On each of the spectra, no signal assigned to $Q^3$ silanol defects (≡Si—OH) was observed at −103 ppm. The peaks displayed by the silicalite particles of Samples I, II, IV and V indicate very low silanol defect concentrations with no distinguishable dependence on particle size.

Example 5

Figure 5:
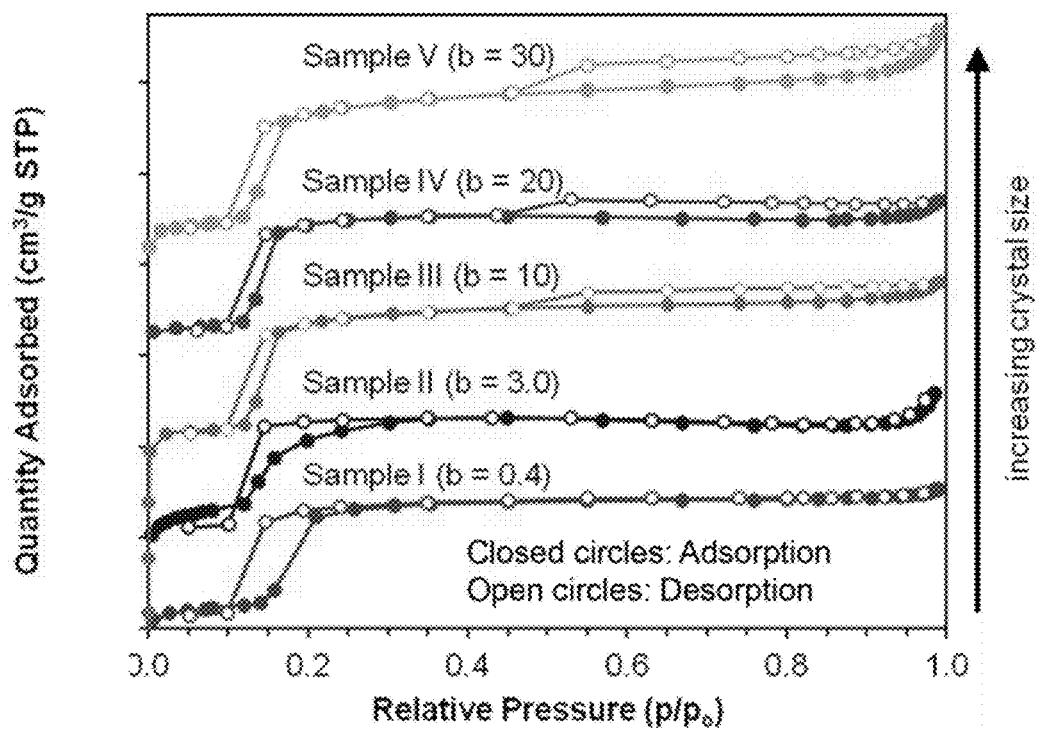
FIG. 5 shows a plot of nitrogen adsorption and desorption isotherms for silicalite particles made according to the present invention.

Nitrogen adsorption and desorption isotherms at 77K, Brunauer-Emmett-Teller (BET) surface areas and pore volumes (t-plot method) were calculated for Samples I-V from $N_2$ physisorption measurements performed on an ASAP 2020 (Micrometrics). Samples I-V were degassed at 200° C. for 18 h within the $N_2$ physisorption apparatus prior to taking measurements. FIG. 5 shows a nitrogen physisorption plot showing the adsorption and desorption isotherms for Samples I-V.

Example 6

Figure 6:
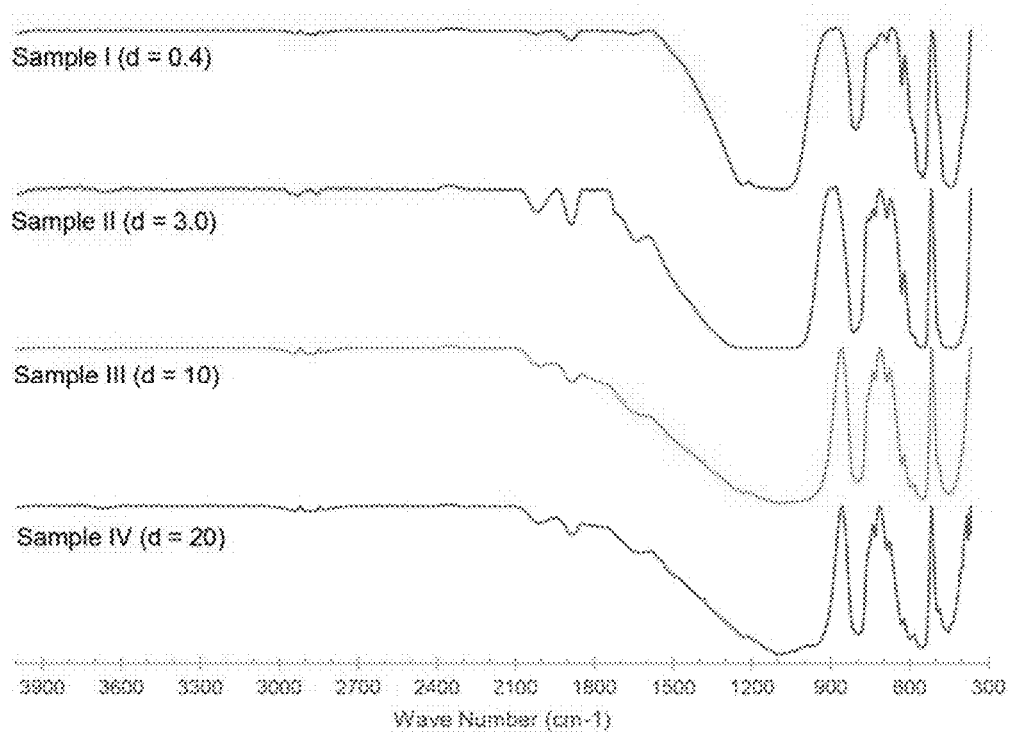
FIG. 6 shows a plot of FT-IR spectra for silicalite particles made according to the present invention.

KBr pellets were prepared using equal amounts of Samples I-IV and analyzed using a Bruker Vertex 80 v FT-IR with wavenumbers from 400 to 4000 cm$^{-1}$. FT-IR spectra of Samples I-IV are shown in FIG. 6.

Example 7

Figure 7:
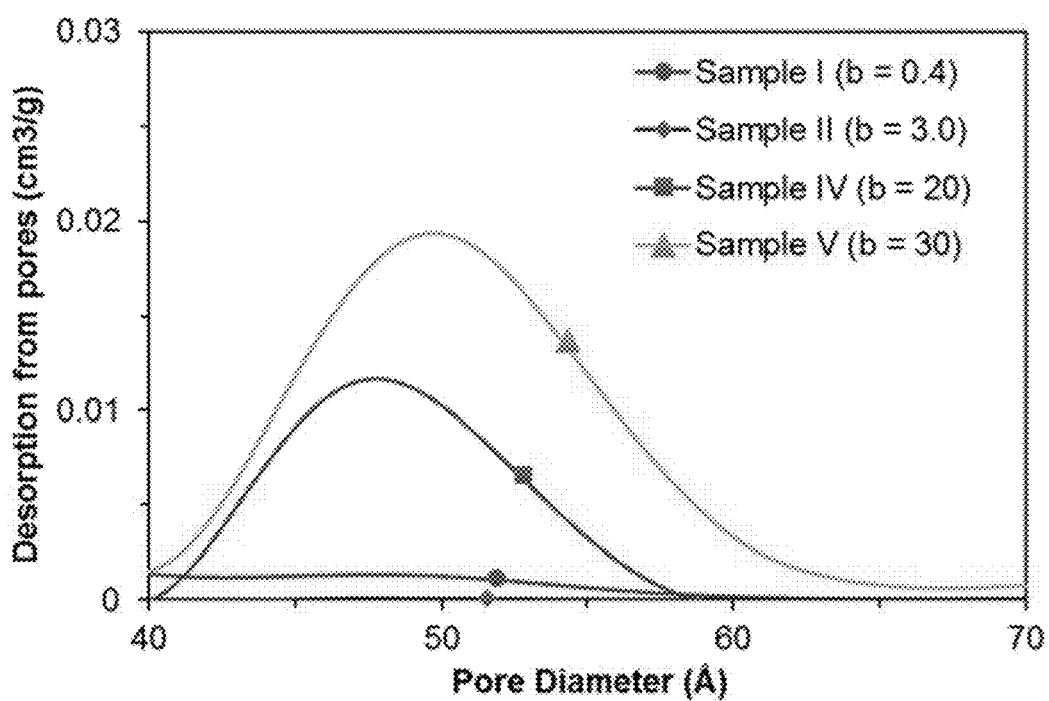
FIG. 7 shows a plot of pore size distribution for silicalite particles made according to the present invention.

Pore size distribution of Samples I, II, IV and V was determined using a simplified Broekoff-de Boer (BdB) pore size analysis method and the Frenkel-Halsey-Hill (FHH) theory for determining the statistical thickness of an adsorbed gas layer. As shown in FIG. 7, increasing average pore size and distribution correlated to increasing crystal size. Pore volume increased as particle height or b-dimension increased. As the distribution of pore volumes for a Sample approaches a normal distribution, as shown in FIG. 7, the percentage of mesopores is greater than for a Sample exhibiting a flat distribution of pore volumes. The pore volumes for silicalite particles of Sample I were below about 0.0025 cm$^3$ per gram.

Example 8

Pure vapor adsorption equilibrium experiments were performed on a VTI-SA vapor sorption analyzer from TA Instruments (New Castle, Del., United States) at 35° C. The vapor activity was controlled automatically by mixing a saturated vapor feed (using $N_2$ as the carrier gas) with a dry $N_2$ stream. The sample "dry mass" was measured under $N_2$ and was at equilibrium before introduction of the vapor to the sample chamber.

FIG. 8 shows isotherms obtained for water uptake by Samples I-V, with lower water uptake correlating with smaller particle size and higher aspect ratio.

FIGS. 9 and 10 show water uptake response to the ratio of particle surface area to mass at an activity of 0.95. The ratio of particle surface area to mass increases as particle size decreases. The calculated values for water uptake indicate that one of skill in the art would expect water uptake values to increase as the ratio of particle surface area to mass increases and particle size decreases, assuming identical pore volumes and framework chemistry. Instead, measured water uptake values for silicalite particles of Samples I-V decreased as particle size decreased.

Figure 11:
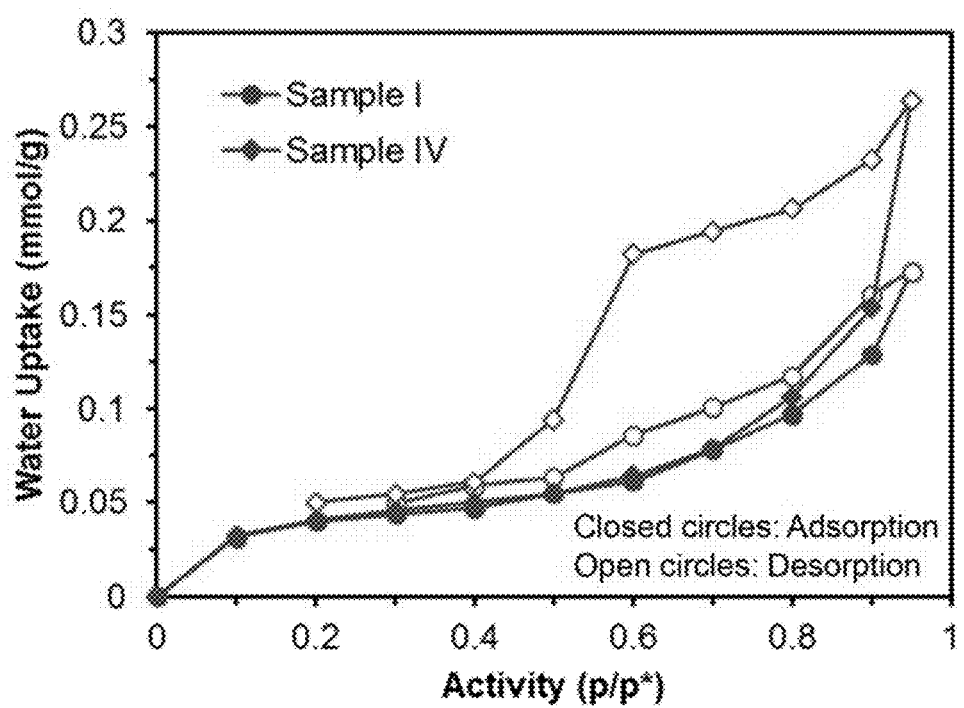
FIG. 11 shows a plot of water adsorption and desorption at 35° C. for silicalite particles made according to the present invention.

FIG. 11 shows adsorption and desorption isotherms for Samples I and IV. Desorption for smaller silicalite particles of Sample I occurred at activities of about 0.8 to about 0.9, while desorption for larger silicalite particles of Sample IV occurred at activities of about 0.4 to about 0.6, indicating an increase in concentration of mesopore-scale defects in the silicalite particles correlating with increasing particle size.

Figure 12:
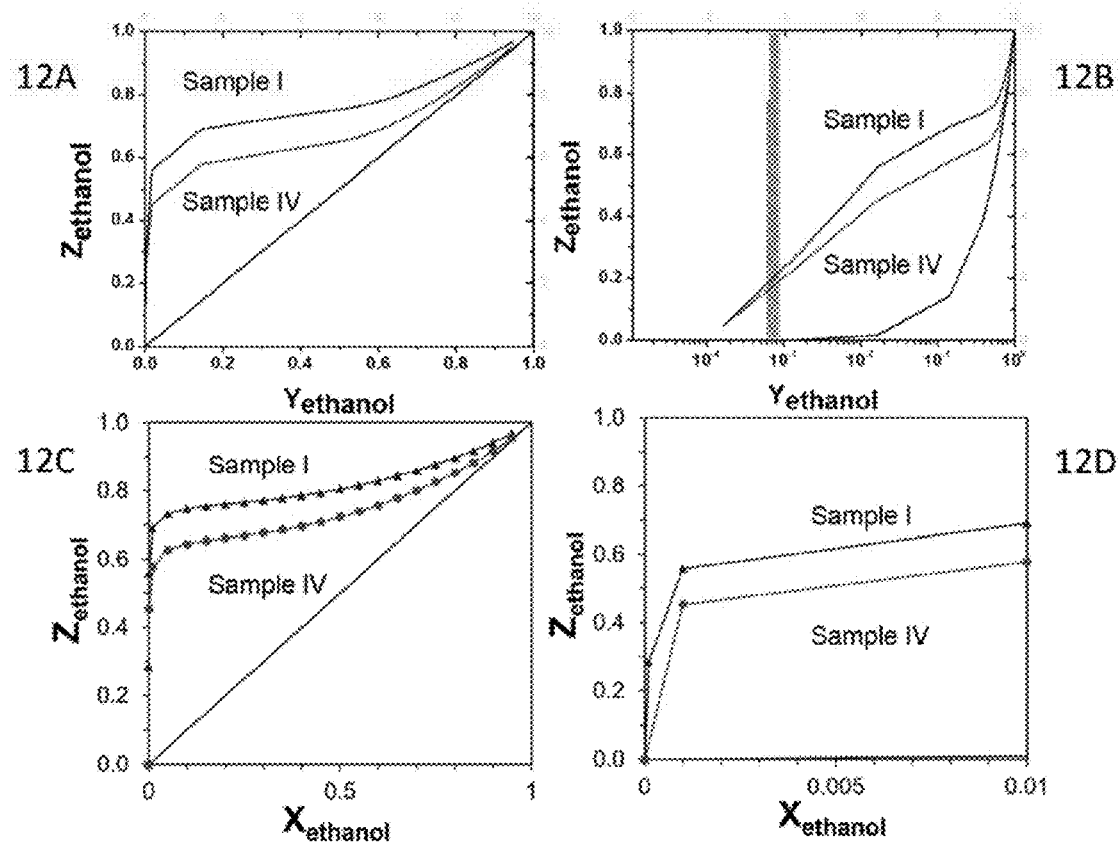
FIGS. 12A-D show plots of IAST predictions for competitive ethanol/water sorption by silicalite particles made according to the present invention. $Y_{ethanol}$ is the mole fraction of ethanol in a vapor-phase ethanol/water mixture, $Z_{ethanol}$ is the mole fraction of ethanol in the adsorbed phase, and $X_{ethanol}$ is the mole fraction of ethanol in a liquid-phase ethanol/water mixture.

FIGS. 12A and 12B show phase diagrams predicted by ideal adsorbed solution theory (IAST) for vapor phase ethanol-water mixtures in equilibrium with Sample I and Sample IV. FIGS. 12C and 12D show IAST-predicted phase diagrams for liquid phase ethanol-water mixtures in equilibrium with Sample I and Sample IV. In IAST, adsorbed phases are assumed to behave as ideal solutions, the standard state is assumed to be the pure adsorbed species at the same temperature and spreading pressure as that of the mixture, and the presence of two adsorbates in a mixed adsorbed phase is assumed not to introduce any non-ideal sorbate-sorbate interaction effects. FIGS. 12C and 12D were determined by assuming that the sorbents are non-wetting when in contact with the liquid mixture.

According to FIGS. 12A and 12B, a vapor feed with an ethanol content of 10$^{-3}$ mol/mol is predicted to have an adsorbed phase ethanol mol fraction of 0.23 mol/mol (230× improvement for Sample I, 180× improvement for Sample IV). According to FIGS. 12C and 12D, a liquid phase feed with an ethanol content of 10$^{-3}$ is predicted to have an adsorbed phase ethanol mol fraction of 0.56 (560× improvement for Sample I, 450× improvement for Sample IV), such that the ethanol product purity for Sample I particles is predicted to be 25% higher than for Sample IV particles.

FIG. 13 shows ethanol selectivity for the silicalite particles of Samples I and IV, as derived from the IAST predictions of FIGS. 12A-12D. The silicalite particles of Sample I exhibit higher ethanol selectivity than the silicalite particles of Sample IV, particularly in a range of ethanol mole fractions from about 0.1 to about 0.5 in a vapor-phase ethanol/water mixture.

Example 9

Figure 14:
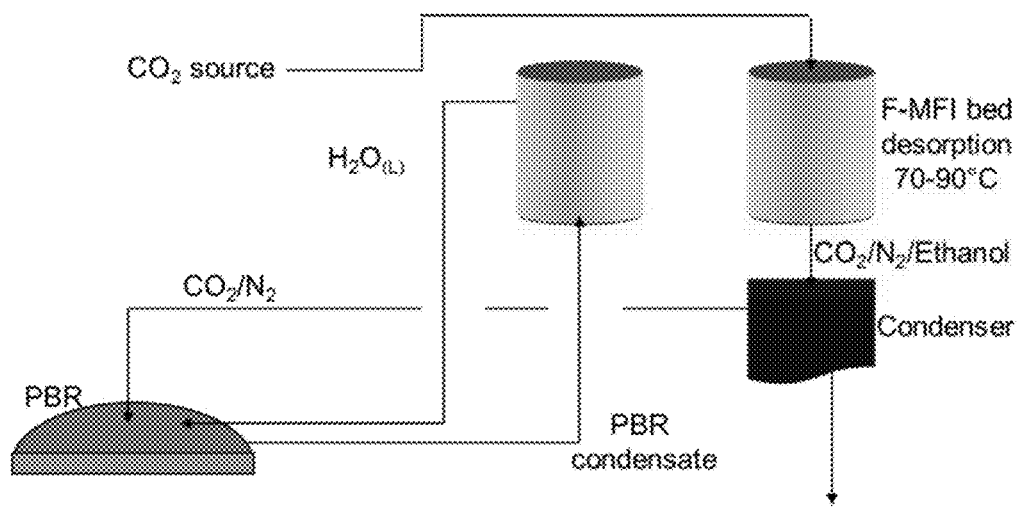
FIG. 14 shows a system incorporating a photobioreactor and a monolith sorbent reactor comprising silicalite particles made according to the present invention.
Figure 15:
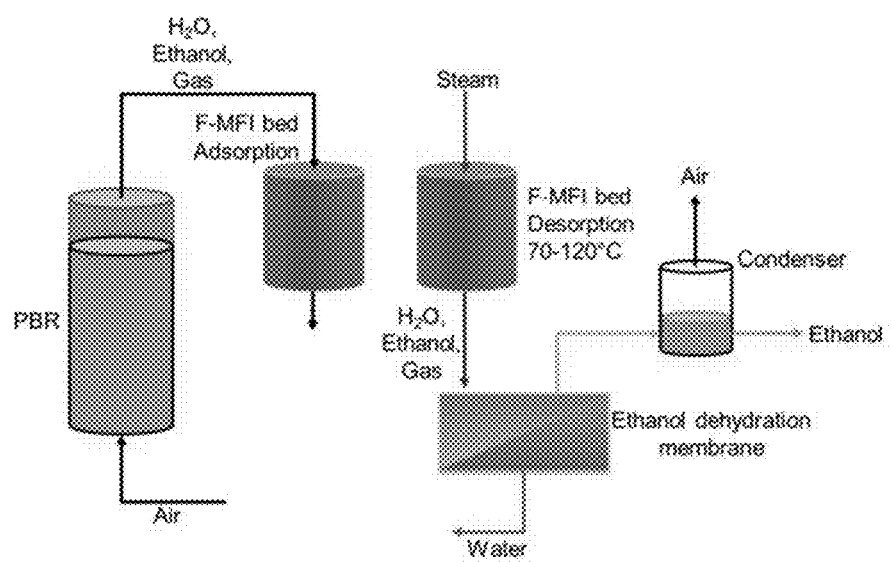
FIG. 15 shows a system incorporating a photobioreactor and a monolith sorbent reactor of silicalite particles made according to the present invention.

FIGS. 14 and 15 illustrate prophetic examples of systems incorporating a photobioreactor and one or more monolith sorbent reactors comprising silicalite MFI particles of Sample I, wherein the monolith sorbent reactors are used to recover ethanol product in liquid phase from a dilute aqueous feed, such as liquid culture medium or condensate from the photobioreactor, or to recover ethanol product from a dilute vapor feed, such as vapor from the photobioreactor.

Figure 16:
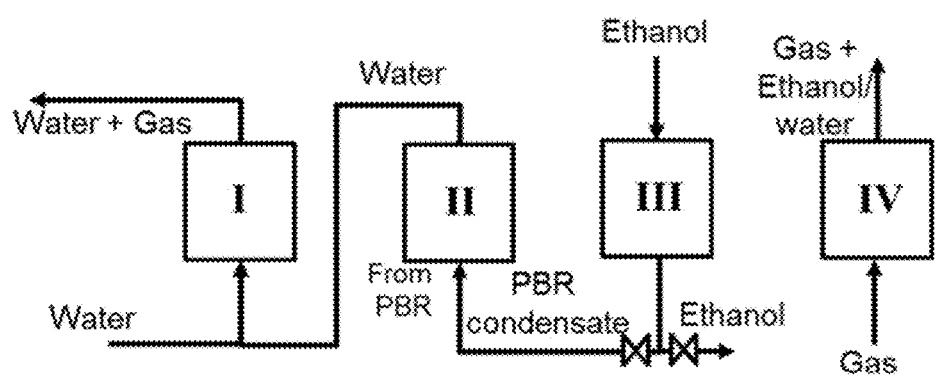
FIG. 16 shows operation of a monolith sorbent reactor comprising silicalite particles made according to the present invention.

FIG. 16 shows the order of operations in the monolith sorbent reactors during operation of the system. A liquid mixture of ethanol and water drawn from a photobioreactor will be introduced to the monolith sorbent reactor (Step II). Interstitial water in the monolith sorbent reactor will be displaced by the ethanol/water solution as it moves through the monolith sorbent reactor, thus producing a pure water stream. As ethanol sorbs into the monolith sorbent reactor, the rejected water proceeds out of the monolith sorbent reactor.

At the end of the adsorption step (Step II), the monolith sorbent reactor is then washed with 1-2 reactor volumes of product ethanol (Step III) to remove the interstitial ethanol/water solution.

After the product wash step (Step III), the monolith sorbent reactor is heated (Step IV), preferably to 70-110° C., in the presence of a gas such as carbon dioxide. A non-polar gas such as carbon dioxide, nitrogen, argon or helium can be selected for use in this step based on its high partition coefficient with an aqueous solution.

The adsorbed mixture of ethanol and water will desorb from the monolith sorbent reactor into the gas phase. The gas phase comprising ethanol can be transferred from the monolith sorbent reactor to a condensing unit in order to condense, capture and further treat the ethanol vapor as a liquid phase product, as shown in FIG. 14. For a 1.5 wt % ethanol feed resulting in a product of 80 wt % ethanol using the system exemplified in FIG. 14, a preliminary estimate of energy consumption is 0.08 MJ required per MJ produced.

Alternatively, the gas phase comprising ethanol can be further refined to remove water impurities using a high temperature ethanol dehydration membrane, for example, as shown in FIG. 15. The configuration shown omits the use of a scrubber between the photobioreactor and the monolith sorbent reactors, as the sorbent of the present invention advantageously rejects both water and air. In an alternative configuration incorporating a scrubber between the photobioreactor and the monolith sorbent reactors, the sorbent of the present invention is washed with the ethanol-enriched stream leaving the scrubber.

The monolith sorbent reactor can then be refilled with an aqueous wash (Step I) in order to "pre-wet" the monolith sorbent reactor in preparation for the next sorption cycle and prevent bypass of the ethanol/water solution in Step II. During this step, gas that was sorbed by the monolith sorbent reactor during the heating step will partition into the aqueous wash. A non-polar gas selected for use in the heating step will have a high partition coefficient with the aqueous wash. Carbon dioxide that is used in the heating step and subsequently partitions into the aqueous wash can be recycled to the photobioreactor for consumption by cyanobacteria or other microorganisms contained in the photobioreactor.

Although the present disclosure has been described in considerable detail with reference to certain embodiments thereof, other embodiments are possible. Therefore, the spirit and scope of the appended claims should not be limited to the description of the embodiments contained herein, and all changes that come within the meaning and range of equivalents are intended to be embraced therein.

What is claimed is:

1. A silicalite particle having a mean height of about 0.2 microns to about 10 microns, mesopore pore volume of less than about 0.0025 cm$^3$ per gram, and water uptake of about 0.20 mmol per gram or less at an activity (p/p*) of 0.98 and 35° C.

2. The silicalite particle of claim 1 further having a MFI structure and a mean aspect ratio of about 5 to about 14.

3. The silicalite particle of claim 2 further having selectivity for ethanol over water of about 190 at an ethanol mole fraction of about 0.2 in a vapor-phase ethanol/water mixture.

* * * * *